United States Patent
Nordquist et al.

[11] Patent Number: 5,704,907
[45] Date of Patent: *Jan. 6, 1998

[54] METHOD AND APPARATUS FOR LOWERING THE INTRAOCULAR PRESSURE OF AN EYE

[75] Inventors: Robert E. Nordquist, Oklahoma City; Bing Li, Edmond, both of Okla.

[73] Assignee: Wound Healing of Oklahoma, Oklahoma City, Okla.

[*] Notice: The term of this patent shall not extend beyond the expiration date of Pat. No. 5,520,631.

[21] Appl. No.: 570,400

[22] Filed: Dec. 11, 1995

Related U.S. Application Data

[63] Continuation-in-part of Ser. No. 279,506, Jul. 22, 1994, Pat. No. 5,520,631.

[51] Int. Cl.$^6$ .................................................. A61M 5/00
[52] U.S. Cl. ............................................................. 604/8
[58] Field of Search ............................. 604/8–10, 294; 623/4–6; 424/427

[56] References Cited

U.S. PATENT DOCUMENTS

| | | | |
|---|---|---|---|
| 3,828,777 | 8/1974 | Ness | 424/19 X |
| 3,915,172 | 10/1975 | Wichterle et al. | |
| 4,060,081 | 11/1977 | Yannes et al. | |
| 4,186,184 | 1/1980 | Zaffaroni | 424/14 |
| 4,457,757 | 7/1984 | Molteno | 604/294 |
| 4,501,263 | 2/1985 | Harbuck | |
| 4,521,210 | 6/1985 | Wong | 604/8 |
| 4,554,918 | 11/1985 | White | 604/10 |
| 4,722,724 | 2/1988 | Schocket | 604/8 |
| 4,729,761 | 3/1988 | White | 604/8 |
| 4,750,901 | 6/1988 | Molteno | 604/8 |
| 4,787,885 | 11/1988 | Binder | 604/8 |
| 4,826,478 | 5/1989 | Schocket | 604/8 |
| 4,853,375 | 8/1989 | Krupin et al. | 514/152 |
| 4,886,488 | 12/1989 | White | 604/9 |
| 4,936,825 | 6/1990 | Ungerleider | 604/8 |
| 4,946,436 | 8/1990 | Smith | 604/8 |
| 4,968,296 | 11/1990 | Ritch et al. | 604/8 |
| 5,041,081 | 8/1991 | Odrich | 604/9 |
| 5,073,163 | 12/1991 | Lippman | 604/9 |
| 5,085,629 | 2/1992 | Goldberg et al. | 606/8 |
| 5,127,901 | 7/1992 | Odrich | 604/9 |
| 5,171,213 | 12/1992 | Price, Jr. | 604/9 |
| 5,178,604 | 1/1993 | Baerveldt et al. | 604/8 |
| 5,338,291 | 8/1994 | Speckman et al. | 604/9 |
| 5,370,607 | 12/1994 | Memmen | 604/8 |
| 5,391,201 | 2/1995 | Barrett et al. | 623/5 |
| 5,395,356 | 3/1995 | King et al. | 606/4 |
| 5,397,300 | 3/1995 | Baerveldt et al. | 604/8 |
| 5,401,508 | 3/1995 | Manesis | 424/427 |
| 5,401,509 | 3/1995 | Robertson et al. | 424/427 |
| 5,401,510 | 3/1995 | Robertson et al. | 424/427 |
| 5,520,631 | 5/1996 | Nordquist et al. | 604/8 |

OTHER PUBLICATIONS

Abstract entitled *Effect of Cellulose Membrane Implants on Glaucoma Filteration Surgery in Rabbits* in vol. 35 No. 4 of *Investigative Opthamology and Visual Science* and Abstract Submission Form.

*Primary Examiner*—Mary Beth Jones
*Attorney, Agent, or Firm*—Head, Johnson & Kachigian

[57] ABSTRACT

A method and apparatus for lowering the intraocular pressure of an eye are provided. The apparatus of the invention is a filtering implant comprising a cellulosic membrane adapted to extend from the anterior chamber of the eye through an opening in the limbus corneae to a drainage area beneath a scleral flap. In its most preferred embodiment, the cellulosic membrane consists essentially of a homopolymer of glucose units connected in a 1,4'-β linkage. The implant is of a planar, generally rectangular shape. The method of the invention involves preparing and implanting the device within the eye such that it extends from the anterior chamber of the eye through an opening in the limbus corneae to a drainage area beneath a scleral flap.

39 Claims, 3 Drawing Sheets

METHOD AND APPARATUS FOR LOWERING THE INTRAOCULAR PRESSURE OF AN EYE

CROSS REFERENCE TO RELATED APPLICATION

This application is a continuation-in-part of application Ser. No. 08/279,506, filed Jul. 22, 1994, now U.S. Pat. No. 5,520,631.

BACKGROUND OF THE INVENTION

1. Technical Field

This invention relates to ophthalmic implants and the manipulation of the intraocular pressure of the eye, and, more particularly, to a new and useful method and apparatus for lowering intraocular pressure by draining aqueous humor from the anterior chamber of the eye and by mechanically inhibiting wound healing at the surgical site.

2. Background

Throughout the United States, Europe and most of the first world countries, glaucoma is the most prevalent sight threatening disease and is, on a world wide basis, responsible for approximately ten percent of all blindness. Glaucoma is an ocular disease where ocular fluids build up in the eye and exert tremendous pressure on the optic nerve, slowly causing irreparable damage as a result of glaucomatous optic neuropathy.

Glaucoma is a significant healthcare problem with immediate and long term ramifications, both physical and financial. Glaucoma is the leading cause of blindness in the United States, where over 300,000 new cases are reported each year. In the U.S. more than 95,000 glaucoma patients lose some degree of sight each year due to the disease, with greater than 5,500 experiencing total blindness. As treatment costs on a per year basis are estimated to be $1.5 billion based upon more than two million annual office visits, the socio-economic impact of glaucoma is significant.

The causes of glaucoma are poorly understood; however, vasomotor and emotional instability, hyperopia, and especially heredity are among the recognized predisposing factors. Along with persons predisposed to glaucoma by virtue of family history, individuals at higher risk of developing glaucoma are those 35 years of age or older or those with diabetes or positive glucose tolerance tests. The disease also strikes African-Americans in disproportionate numbers. They are four to five times more likely to develop glaucoma and are up to six times more apt to suffer a complete loss of sight.

The increased intraocular pressure incident to glaucoma is related to an imbalance between production and outflow of aqueous humor, the watery fluid that fills the anterior and posterior chambers of the eye. Aqueous humor is secreted by the ciliary processes of the eye, and passes through the posterior chamber and the pupil into the anterior chamber where it is reabsorbed into the venous system at the iridocorneal angle by way of the sinus venosus, also called the canal of Schlemm. Obstruction of aqueous humor outflow appears to be mainly responsible for elevated intraocular pressures.

The aim of current glaucoma treatment is the prevention of optic nerve damage and vision loss by lowering intraocular pressure. The search for better treatment regimens has moved back and forth between pharmaceutical and surgical methods as the first line of treatment.

In the United States, pharmaceuticals have been traditionally utilized as an initial response. Common pharmaceutical treatments for glaucoma include the systemic use of carbonic anhydrase inhibitors or topical applications of pilocarpine, timolol maleate, betaxolol HCl, levobunolol, metipranolol, epinephrine, dipivefrin, demecarium bromide, and echothiophate iodide. But, as is the case with most significant chemical therapies, the side effects of these medications may be severe while the treatment's efficacy is variable. Some of the drugs have unwanted systemic effects on cardiovascular functions and blood pressure, result in headaches or nausea, or cause ocular burning and irritation. However, the most frequent and perhaps most serious drawback to drug therapy is that patients, especially the elderly, often fail to correctly self-medicate. They forget to take their medication at the appropriate times or else administer the eyedrops improperly, resulting in under or over dosing. Because the effects of glaucoma are irreversible, when patients dose improperly—allowing ocular concentrations to drop below the appropriate therapeutic level—further permanent damage to vision occurs.

In Europe, where for many years there has been a strong focus on cost containment, surgery is the preferred approach. This is also the case in the United States when medication fails to control intraocular pressure or visual fields show progressive defects. It has been reported that in 1993 over 1,152,000 operations for regulating intraocular pressure were performed in the U.S. alone.

Glaucoma filtration surgery historically has been the most widely practiced procedure used in severe glaucoma cases. The fundamental principle of this surgery is to create an opening, or fistula, at the limbal region of the eye to facilitate the drainage of the aqueous humor, bypassing the pathological blockage in the anterior chamber angle. There are two basic approaches currently in use. In a full-thickness filtration procedure, a full-thickness sclerostomy is made, connecting the anterior chamber directly to the subconjunctival space. The main advantage of this procedure is the significantly lower intraocular pressures achieved postoperatively. However, because of its complications, this surgery is less frequently used than the second type of surgery, the trabeculectomy. In the trabeculectomy, a sclerostomy is performed under a scleral flap. This flap is then sutured back to its original bed in an attempt to minimize aqueous outflow runoff. The advantage of the trabeculectomy under the scleral flap is the tamponate effect provided by the resutured sclera causing a subsequent reduction of aqueous flow-through. Unfortunately, although this procedure provides short-term postoperative stability, final intraocular pressure levels are usually higher than those seen after full-thickness filtration, and the long term success rate is lower.

A major problem with both these approaches, and glaucoma filtration surgery in general, is the body's natural healing process. Glaucoma filtration surgery differs from most surgical procedures in that inhibition of wound healing is desirable to achieve surgical success. When normal wound healing occurs, filtration rates decrease and intraocular pressures rise, making necessary the inhibition of the healing response. Surgical failures occur most frequently due to an overwhelming wound healing response and scarring at the filtration site. Histological studies of human and lab animal surgeries suggest that failure of glaucoma filtration surgery is associated with the presence of dense fibrovascular connective tissue around the surgical site. This prevents diffusion of the aqueous humor from the subconjunctival space.

Since the turn of the century many efforts have been made to facilitate aqueous outflow and defeat the healing process by the insertion of devices in the surgical fistula. These devices have varied widely in size, material composition and design, one of the first being the horse hair implant of Rabbett and Moreau in 1906. Over time, aqueous shunts have become an increasingly popular and effective means of lowering intraocular pressure. Among the more recent devices, translimbal equatorial shunts have proven most effective. Examples of such devices include those disclosed in United States patents granted to Molteno (U.S. Pat. No. 4,457,757 and 4,750,901), Oldrich (U.S. Pat. No. 5,041,081 and 5,127,901), and Baerveldt et al. (U.S. Pat. No. 5,178,604). Molteno's devices generally consist of ridged plates having drainage tubes for insertion into the anterior chamber of the eye. Odrich's patents disclose two ophthalmic implants for relieving pressure in the anterior chamber, both having one-way flow resisting valves, and residing under the conjunctiva. Baerveldt's apparatus comprises an elastomeric plate having a drainage tube tunneled through Tenon's capsule and the cornea and inserted into the anterior chamber. Virtually all conventional glaucoma aqueous drainage implants are designed to allow aqueous flow around their surface or to conduct the aqueous through a hollow tube either directly into a vein or bleb or to a large episcleral plate that will deposit aqueous in the posterior conjunctiva between the muscles.

Conventional aqueous shunts, however, are plagued by several peculiarities, including foreign body reactions and inflammation, as well as obstruction and infection. A major disadvantage of current open tube aqueous drainage devices is excessive aqueous drainage in the immediate postoperative period resulting in a flat anterior chamber and potential choroidal detachment. Profound hypotony, possibly leading to phthisis bulbi, is also a substantial risk. Excessive post-operative aqueous flow also causes expansion of the fibrous capsule beneath the rectus muscles of the eye. This mass effect stretches and tightens the muscles inducing heterotropia and motility restriction into the quadrant of the implant.

A mass effect also may be exerted simply by the bulky presence of the device itself beneath the muscle causing restriction of eye movement, scleral erosion, changes in eye curvature, or damage to adjacent vasculature and tissue. This is particularly true of rigid plastic or metal implants having valves. They tend to be large and complex in design. Other problems involve friction and wear imparted to the scleral flap by implanted devices, irritation of the iris endothelium caused by placement of implants into the anterior chamber, and aggravation produced by chronic forward and backward movement of the implants. Some glaucoma filtration surgeries also require the performance of peripherial iridotomies, wherein a transverse division of some of the fibers of the iris is performed to create a communication between the anterior chamber and the posterior chamber.

In spite of these shortcomings, aqueous drainage devices have been successful in many cases, but the operative procedure remains challenging and significant complications are not unusual.

It is thus an object of the present invention to provide a method and apparatus for lowering the intraocular pressure of an eye and mechanically inhibiting wound healing at the surgical site without producing a foreign body reaction, inflammation, obstruction, or infection.

Another object of the invention is to design and construct an intraocular implant that is pliable so as to fit the contours of the eye, that is soft enough to avoid scleral erosion, inducement of undesirable changes in eye curvature, or damage to adjacent vasculature and tissue, but that is resilient enough to maintain its shape and thickness. A like object is that the construction of the implant solves problems of friction and wear imparted to a scleral flap, irritation of the iris endothelium, and aggravation produced by implant movement.

A further object of the invention is to provide a device that naturally regulates the flow of aqueous humor by mimicking the trabecular meshwork, the device having a microstructure that allows drainage but never results in a post-surgical hypotony as seen with hollow tube devices.

Yet another object of the invention is to supply an intraocular implant that is small and simple, that has no valves, tubes or pressure sensing mechanisms, so as to avoid mechanical failure and allow for unobstructed eye movement.

A still further object of the invention is to furnish a method for surgically implanting an intraocular filtration device, which procedure is relatively simple and has few complications.

SUMMARY OF THE INVENTION

These and other objects and advantages are achieved by the present invention. The apparatus of the invention is a filtering implant comprising a cellulosic membrane adapted to extend from the anterior chamber of the eye through an opening in the limbus corneae to a drainage area beneath a scleral flap. In its most preferred embodiment, the cellulosic membrane consists essentially of a homopolymer of glucose units connected in a 1,4'-β linkage. The implant is of a planar, generally rectangular shape.

In accordance with one aspect of the invention, the implant is described as having a proximal end and a distal end, the margins of the proximal end being altered so as to form a foot portion for placement in the anterior chamber of the eye and a body portion for burial beneath the scleral flap. Two opposing rectangular notches are preferably used to alter the margins of the proximal end so as to demarcate the foot portion from the body portion. While the dimensions of the implant may be altered to take into account individual patient variables, the preferred implant is about 50 microns thick, and has an overall length of 8–10 mm and an overall width of about 6 mm. A center cut extends axially from the proximal end of the implant through the foot portion of the device toward the distal end to facilitate insertion of the implant through the limbal opening.

In accordance with another aspect of the invention, at least one curved, resilient arm member may be used to maintain the post-surgical position of the implant. In one embodiment, the foot portion of the device is provided with such an arm member. In another embodiment, the proximal end of a planar, generally rectangular shaped implant has an integrally formed key projecting therefrom for placement through the limbal opening and into the anterior chamber. The key has at least one curved, resilient arm member radially extending therefrom for abutting the inner surface of the limbus corneae after implantation so as to maintain the post-surgical position of the implant. The arm member may comprise a polypropylene material glued to the key with a surgical adhesive or a polymethylacrylate material polymerized integrally to the key.

The method of the invention involves preparing and implanting the device described above, and in further detail hereinbelow, within the eye such that it extends from the anterior chamber of the eye through an opening in the limbus corneae to a drainage area beneath a scleral flap. The implant is die cut or stamped from a cellulosic membrane stock into a planar, generally rectangular shape having a proximal end terminating in a foot portion or key and a distal body portion. The implant is thoroughly rinsed in distilled water. The device is then heated to 100° C. for 30 minutes in a solution of 2% sodium bicarbonate and 1% ethylenediaminetetraacetic acid, followed by cooling at 4° C. in balanced saline solution. After rinsing again in a balanced saline solution, the implant may be placed in a container of a solution of sterile de-ionized water and sterilized by autoclave for storage until use. At the time of surgery, the implant is recovered from storage and is appropriately implanted within the eye.

Implantation of the device involves opening the conjunctiva such that the sclera and the limbus corneae are accessible. A section of the sclera is dissected to obtain a scleral flap, and a limbal opening is made through the limbus corneae and into the anterior chamber. The implant is folded along its center cut so that the foot portion is easily insertable through the limbal opening into the iridocorneal angle of the anterior chamber. The body portion of the implant is set into a surgical bed entirely beneath the scleral flap, after which the scleral flap is sutured closed. The conjunctiva is likewise sutured shut.

DETAILED DESCRIPTION OF THE PREFERRED EMBODIMENT

The Implant

The present invention comprises an implant for lowering the intraocular pressure of an eye made from a cellulosic membrane. The implant is shaped and adapted to extend from the anterior chamber of the eye through an opening in the limbus corneae to a drainage area beneath a scleral flap.

In nature, cellulose exists as a series of extremely high molecular weight polymers which associate together in an ordered state. Native cellulose is extraordinarily insoluble in water as well as most organic solvents. Until now, the principal applications of cellulosic membranes have been in the areas of pharmacology, clinical and biological chemistry, and food chemistry. Cellulosic membranes have shown themselves especially useful in the field of dialysis. The cellulosic membrane stock used in connection with the present invention consists essentially of a homopolymer of glucose units connected in a 1,4'-β linkage. An example of an acceptable, commercially available cellulosic membrane for use in connection with the present invention is SPECTRA/POR, manufactured by Spectrum Medical Industries, Inc. of Los Angeles.

That the implant is composed of a cellulosic material is critical. This makes the implant soft enough to avoid eye tissue damage, flaccid enough to be easily seated in a scleral bed and to conform to the curvature of the surgical sight, and strong enough to keep the surgical fistula open permanently. Additionally, because of its composition, the implant is easy to size and to modify such that the extrinsic ocular motility is not disturbed subsequent to the implant procedure. Further, as the implant is constructed from cellulosic material, its surface is so smooth as to resist cellular attachment and invasion. The implant is non-absorbable and stable at body temperature due to its composition.

Figures 1, 2:
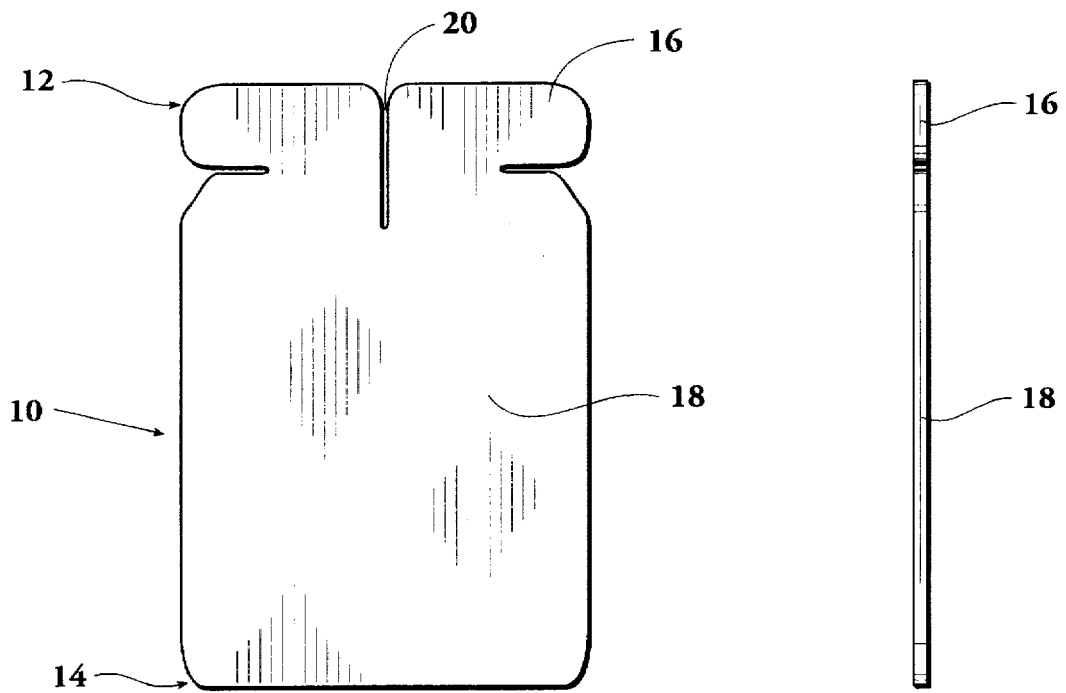
FIG. 1 is a from elevational view of the preferred implant of the present invention.
FIG. 2 is a side elevational view of the preferred implant.

Referring now to FIGS. 1 and 2, there is shown the preferred embodiment of the implant. The implant, indicated by the reference numeral 10, is of a planar, generally rectangular shape. The implant 10 has what can be called a proximal end 12 and a distal end 14. The margins (or periphery) of the implant 10 approaching the proximal end 12 are altered so as to form or demarcate a foot portion 16 for placement in the anterior chamber of the eye and a body portion 18 for burial beneath a scleral flap. As shown in FIG. 1, the margins of the implant 10 toward the proximal end 12 are indented inward toward the longitudinal axis of the implant 10 to define the foot portion 16 from the body portion 18. There is a center cut 20 axially extending from the proximal end 12 of the implant 10 toward the distal end 14, such that the foot portion 16 can be folded for easy placement within the eye.

Figure 3:
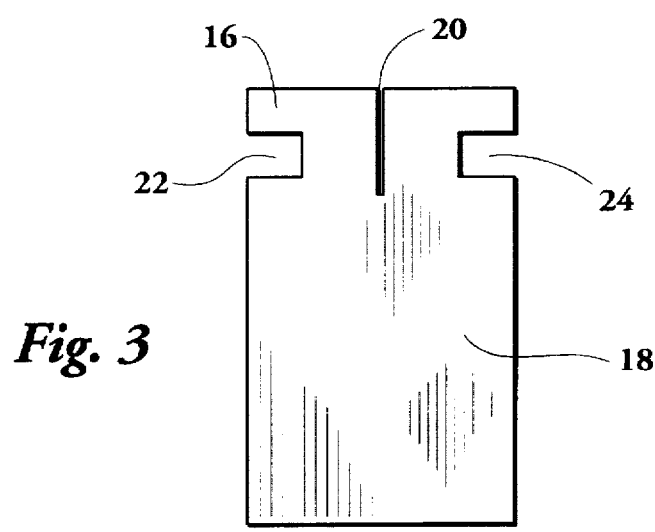
FIG. 3 shows a die cut implant of a shape similar to FIG. 1.

The implant 10 is preferably constructed by die cutting a cellulosic membrane stock into the shape as shown in FIG. 3. Evident in FIG. 3 are two opposing rectangular notches 22, 24 used to alter the margins toward the proximal end 12 of the implant 10 so as to form the foot portion 16 and body portion 18. The phantom line 26 shown in FIG. 3 indicates where the center cut 20 will be made. Upon hydration, the implant 10 shown in FIG. 3 takes a shape similar to that shown in FIG. 1.

After the implant 10 is formed from a cellulosic membrane stock into its preferred shape, it is prepared for use. One manner of preparing the implant 10 for use includes first rinsing it in distilled water. It is then heated to 100° C. for 30 minutes in a solution of 2% sodium bicarbonate and 1% ethylenediaminetetraacetic acid, followed by cooling at 4° C. in balanced saline solution. After rinsing again in a balanced saline solution, the implant may be placed in a container of a solution of sterile de-ionized water and sterilized by autoclave for storage until use. At the time of surgery, the implant 10 is implanted within the eye such that the foot portion 16 extends into the anterior chamber of the eye through an opening in the limbus corneae and the body portion 18 is buried beneath a scleral flap, all as described hereinbelow. Treating the cellulosic membrane prior to die cutting it to form is acceptable, and is discussed below in connection with the experimental studies reported, but it is now preferred that the membrane be cut prior to treatment.

Before discussing the preferred dimensions of the implant 10, it should be understood that the dimensions are alterable to the extent necessitated by individual patient variables such as the size of the eye, amount of pressure in the eye, and the age of the patient. The implant 10 is between 25 microns and 150 microns thick, and is of a preferred thickness of approximately 50 microns (0.05 mm). The overall length of the implant 10 is approximately 8–10 mm, while the overall width is approximately 6 mm. The rectangular notches 22, 24 shown in FIG. 3 are preferably about 1.5 mm in width and 1 mm in length. The foot portion 16 in the preferred embodiment has a length of approximately of 1 mm and a width of about 6 mm. In the preferred embodiment, the body portion 18 of the implant 10 has a length of approximately 8 mm and a width of approximately 6 mm.

Figures 4, 5:
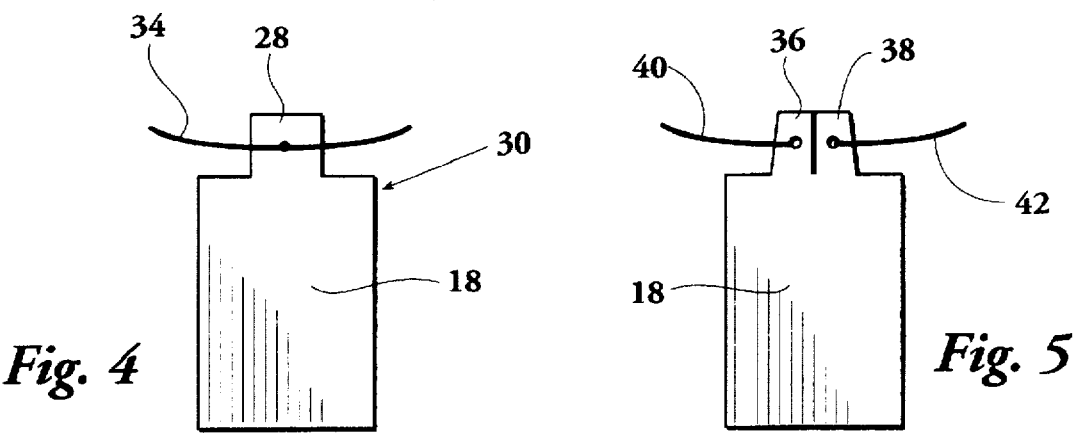
FIG. 4 is a front elevational view of a first alternate implant.
FIG. 5 is a front elevational view of a second alternate implant.

FIGS. 4 and 5 show two alternate embodiments of the present invention. Both alternate embodiments are similarly constructed from a cellulosic membrane consisting essentially of a homopolymer of glucose units connected in a 1,4'-β linkage, and both can still be said to be of a planar, generally rectangular shape and have a proximal end and a distal end. Looking now at FIG. 4, there is shown an integrally formed key (or tab) 28 projecting from the proximal end 30 of the device for placement through a limbal opening and into the anterior chamber of the eye. The key 28 has a curved, resilient arm member 34 radially extending therefrom. The shape and dimension of the key 28 prevents iris touch. The function of the arm member 34 is to maintain the post-surgical position of the implant.

FIG. 5 shows an implant similar to that shown in FIG. 4, but wherein a center cut divides the key into a first piece 36 and a second piece 38, such that the key can be folded for easy insertion. A first curved, resilient arm member 40 extends radially from the first piece 36, while a second curved, resilient arm member 42 extends radially from the second piece 38. In combination the arm members 40, 42 function to maintain the post-surgical position of the implant.

The arm members 34, 40, 42 of FIGS. 4 and 5 may be made of a polypropylene material which can be glued to the key with a surgical adhesive or a polymethylacrylate material or other substance which can be polymerized integrally to the key. An appropriate class of surgical adhesives are cyanoacrylate compositions. Alternatively, the foot portion 16 or key 28 could be provided with an eyelet or hole, such as by contact with a hot wire, and an arm member 34, 40, 42 could be threaded therethrough. The arm members 34, 40, 42 may be manipulated by the surgeon during implantation to fit through the limbal opening whereupon they spring out to abut the inner surface of the limbus corneae, thus preventing the implant from backward displacement.

The Procedure

Figure 6:
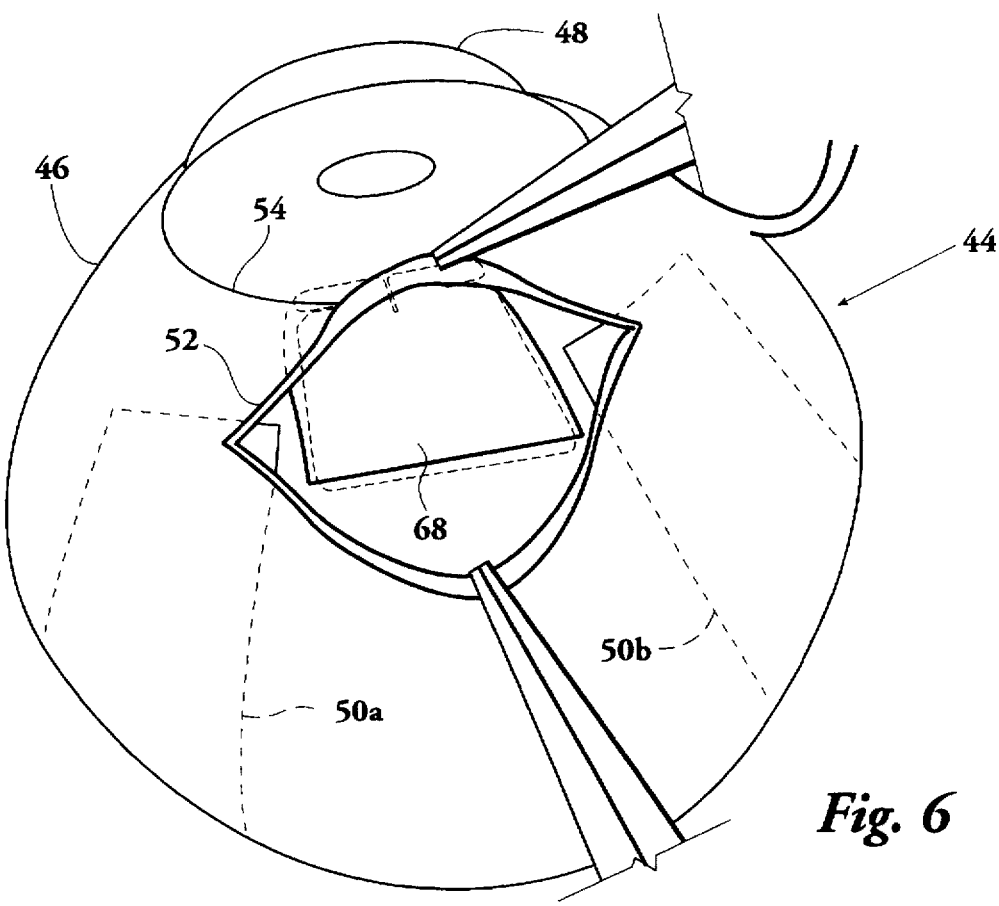
FIG. 6 is a perspective view of the preferred implant as implanted into an eye in accordance with the method of the invention.
Figure 7:
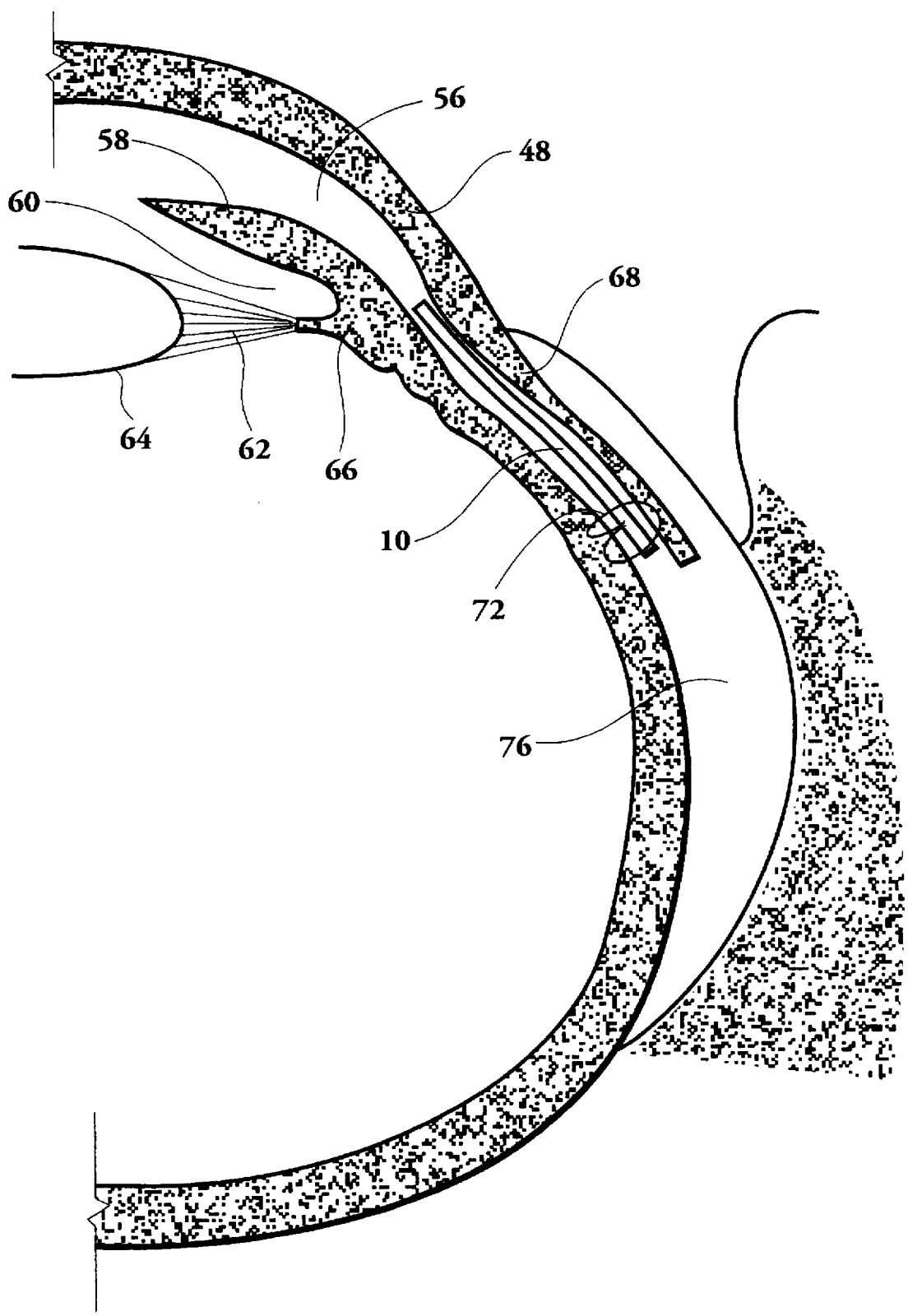
FIG. 7 is a cross-sectional view of the preferred implant after implantation.

The implantation procedure will be described first in connection with FIG. 6, where an eye 44 is shown in a perspective view taken during a surgical filtration procedure, and FIG. 7, which shows a cross-section of the eye 44 after the performance of the implantation procedure.

The sclera 46 and cornea 48 form the external tunic of the eye. They are essentially fibrous in structure, the sclera 46 being opaque and forming the posterior five-sixths of the globe, and the cornea 48 being transparent and forming the remaining one-sixth. The sclera 46 serves to maintain the form of the globe of the eye 44 while the cornea 48 facilitates the transmission of light to the inner eye and protects, as a cover, the structures of the inner eye. The external surface of the sclera 46 is of a white color and is quite smooth, except at the insertion points of the rectus muscles 50a–b. The anterior part of the sclera 46 is covered by the conjunctival membrane 52, also called the conjunctiva. The conjunctiva 52 is the mucous membrane of the eye. It lines the inner surface of the eyelids, where it is thick, opaque, and highly vascular, and is reflected over the fore part of the sclera 46 and cornea 48. Upon the sclera 46, the conjunctiva 52 is loosely connected to the globe of the eye 44 where it has become thinner, transparent, and only slightly vascular. Upon the cornea 48, the conjunctiva 52 consists only of epithelium, constituting the anterior layer of the cornea, known as the corneal epithelium. The sclerocorneal junction is known as the limbus corneae 54. This is where the margin of the cornea 48 is overlapped by the sclera 46. The anterior chamber 56 is the space bounded in front by the cornea 48 and behind by the iris 58. The posterior chamber 60 is a narrow chink between the peripheral part of the iris 58, the suspensory ligament 62 of the lens 64 and the ciliary processes 66. The aqueous humor completely fills both the anterior chamber 56 and posterior chamber 60. The aqueous humor is little more than water in composition, as less than one-fiftieth of its weight is solid matter, that being chiefly sodium chloride.

Now focusing on FIGS. 6–9, in the preferred method of the invention the eye 44 is anesthetized with a retrobulbar injection of 1.5–2.0 ml of lidocaine or procaine or an effective amount of another suitable agent. If stabilization of the eye 44 during surgery is desired, such is accomplished with a bridle suture using 4/0 silk on the superior rectus. In general terms, the conjunctiva 52 is opened such that the sclera 46 and the limbus corneae 54 are accessible. A section of the sclera 46 is dissected to obtain a scleral flap 68, and a limbal opening is made through the limbus corneae 54 and into the anterior chamber 56. The implant 10 is folded along its center cut 20 so that the foot portion 16 is easily insertable through the limbal opening into the iridocorneal angle of the anterior chamber 56. The body portion 18 of the implant 10 is set into a surgical bed 70 entirely beneath the scleral flap 68, after which the scleral flap 68 is sutured closed. The conjunctiva 52 is likewise sutured shut.

In more particularity, the preferred method includes making an 8 mm cord length conjunctival incision 8–10 mm posterior to the surgical limbus in the desired quadrant. A conjunctival flap is formed by dissection of the conjunctiva from Tenon's capsule. Tenon's capsule is dissected from the episclera, beginning with an incision at the site of the conjunctival incision. The dissection is then extended forward to very near the limbus corneae 54.

Next, the perimeter of the intended scleral flap 68 is cauterized. The intended scleral flap 68 should measure approximately 6–8 mm in length and 6 mm in width. The margins of the scleral flap 68 are outlined with partial thickness incisions. Starting posteriorly, a 50–70% thickness of the scleral flap 68 is dissected anteriorly, extending into clear cornea 48 approximately 2 mm. Again, the scleral flap 68 should be generally rectangular in shape and measure 6–8 mm long by 6 mm wide.

The anterior chamber 56 is entered just behind the scleral flap 68. A fistula is created by completing the formation of the anterior and lateral margins of this deep limbal incision. It is preferred that the fistula measure about 0.5–1 mm high by 3 mm in width so as to form a window for the insertion of the foot portion 16 of the implant 10.

Figure 8:
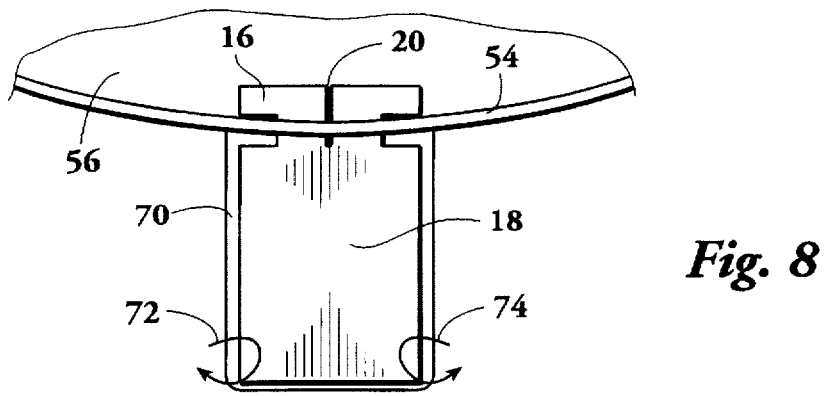
FIG. 8 is a top perspective view of the preferred implant as seated in a scleral bed (the scleral flap not shown).
Figure 9:
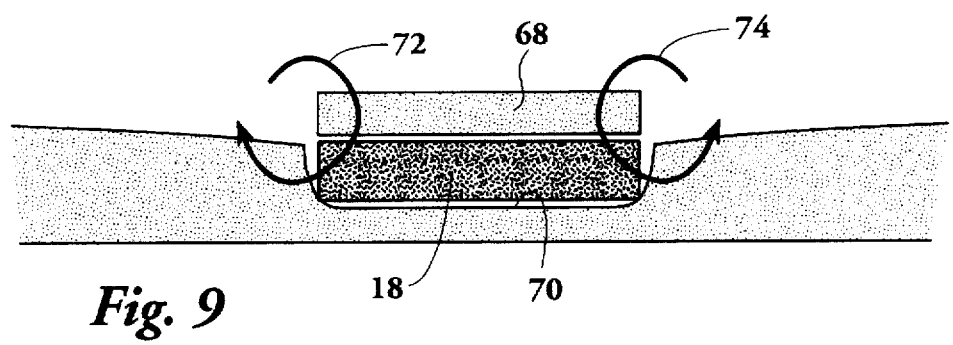
FIG. 9 is a sectional end view of the preferred implant after implantation.

The foot portion 16 or key 28 of the implant 10 is then passed through the fistula into the iridocorneal angle of the anterior chamber 56. The body portion 18 of the implant 10 is buried entirely beneath the scleral flap 68 in the scleral bed 70. The scleral flap 68 and implant 10 are tightly sutured (as shown in FIGS. 7–9) to the scleral bed 70 with two to four 8/0 chromic collagen sutures 72, 74. Tenon's capsule and the conjunctiva 52 are closed separately with a single 6/0 nylon or silk suture.

A filter bleb 76 is formed in a space under the conjunctiva 52 as a result of the implantation of the implant 10. Though it is solid, the implant 10 diffuses water such that the aqueous humor in the anterior chamber 56 passes through the implant 10 into the filter bleb 76 to be disseminated in the sclera 46 and absorbed by the body. A small amount of aqueous humor may also pass through the conjunctiva 52. Similar to a dialysis membrane, the implant 10 functions to allow the passing of fluids without permitting the leaching of proteins or other particulates from the aqueous humor.

rabbits in a preliminary trial. The foot of the implant was passed into the anterior chamber of the eye through a limbal opening and the body portion was buried beneath a scleral flap. This new procedure significantly lowered the intraocular pressure in all experimental rabbit eyes as shown in Table 1 below. Table 2 shows a repeated measures analysis of variance for data presented in Table 1.

TABLE 1

IOP difference (experimental/control) average over study period

| Rabbit | | Baseline | Post-op Day 1–3 | Post-op Day 4–7 | Post-op Day 8–15 | Post-op Day 16–30 | Post-op Day 31–70 |
|---|---|---|---|---|---|---|---|
| 1. | Exper. | 18.7 ± 0.5 | 11.3 ± 1.7 | 12.3 ± 1.3 | 17.6 ± 1.8 | 13.1 ± 4.6 | 13.0 ± 4.4 |
|  | Control | 19.7 ± 1.2 | 10.3 ± 3.0 | 23.3 ± 1.0 | 22.8 ± 4.3 | 19.1 ± 2.8 | 19.9 ± 3.64 |
| 2. | Exper. | 20.0 ± 0 | 12.3 ± 1.9 | 12.0 ± 0 | 15.25 ± 1.0 | 16.9 ± 2.4 | 16.0 ± 2.7 |
|  | Control | 25.3 ± 0.5 | 27.3 ± 3.3 | 22.5 ± 1.8 | 22.1 ± 1.5 | 20.6 ± 1.7 | 21.1 ± 2.5 |
| 3. | Exper. | 22.7 ± 0.5 | 18.0 ± .08 | 13.1 ± 0.9 | 14.25 ± 1.4 | 14.8 ± 3.3 | 15.0 ± 2.91 |
|  | Control | 21.0 ± 0 | 18.7 ± 0.5 | 17.5 ± 2.1 | 17.8 ± 1.8 | 18.1 ± 2.5 | 18.7 ± 2.6 |
| 4. | Exper. | 23.0 ± 0.5 | 16.0 ± 1.4 | 16.0 ± 0.7 | 16.9 ± 0.9 | 16.1 ± 1.4 | 16.0 ± 1.2 |
|  | Control | 23.0 ± 0 | 12.0 ± 2.9 | 17.5 ± 3.8 | 23.0 ± 6.7 | 23.5 ± 4.2 | 22.4 ± 4.9 |
| 5. | Exper. | 24.7 ± 0.5 | 16.3 ± 1.7 | 13.0 ± 1.2 | 15.8 ± 2.6 | 16.0 ± 1.4 | 14.0 ± 3.1 |
|  | Control | 24.7 ± 0.5 | 14.3 ± 2.0 | 17.5 ± 3.2 | 21.4 ± 4.4 | 21.5 ± 2.2 | 20.1 ± 3.6 |
| 6. | Exper. | 22.7 ± 0.5 | 14.7 ± 0.5 | 12.5 ± 1.1 | 13.0 ± 2.7 | 14.4 ± 1.8 | 12.0 ± 3.07 |
|  | Control | 22.7 ± 0.5 | 14.7 ± 2.5 | 16.3 ± 2.8 | 16.5 ± 4.1 | 17.6 ± 2.6 | 18.8 ± 4.43 |
| Group Means 1 S.D. | | | | | | | |
| Exper. | | 22.0 ± 2.2 | 14.8 ± 2.6 | 13.2 ± 1.5 | 15.5 ± 1.7 | 15.2 ± 1.4 | 14.3 ± 1.6 |
| Control | | 22.7 ± 2.1 | 16.2 ± 6.1 | 19.1 ± 3.0 | 20.6 ± 2.8 | 20.1 ± 2.2 | 20.2 ± 1.4 |
| Paired t-Test Results | | | | | | | |
| d | | −0.7667 | −1.4500 | −5.9500 | −5.1167 | −4.8500 | −5.8333 |
| t− | | −0.7872 | −0.5193 | −3.7597 | −9.2054 | −6.9298 | −11.6254 |
| p= | | 0.4668 | 0.6257 | 0.0132 | 0.0003 | 0.0010 | 0.0001 |

Animal Studies

Experiments were conducted on the present invention to test its efficacy. The invention proved to be successful. A first rabbit study, Rabbit Study No. 1, compared a control eye, which was treated with a normal filtering surgery, with the experimental eye treated in accordance with the invention through 70 days. The experiment started with ten animals. Four were terminated during the study for histological samples, while the other six finished the full 70 days of the experiment. After the first four days postsurgery, the difference between the control and experimental group had a p-value of 0.01, and with time the difference was even more significant.

Rabbit Study No. 2 was a year long comparison between an eye treated in accordance with the present invention and a normal untreated control eye. After the first week the difference between treated and control groups was so sound that many intervals had differences significant to <0.00000. The least significant period was the last week of readings, which were significant to the p-value of 0.00018.

A simple cat experiment was also run in which one glaucomatous eye of a cat was implanted in accordance with the invention and followed with the untreated control for 29 weeks. After this time, the second eye was implanted and both eyes continued to be monitored for intraocular pressure and clarity. Again, the surgeries were successful.

Rabbit Study No. 1

The proposed glaucoma filtration procedure was performed utilizing the implant of the present invention in six

TABLE 2

Repeated measures analysis of variance for data presented in Table 1

| Data included in Model | Mean IOP (Treatment) | | P Values | |
|---|---|---|---|---|
| | | Treatment | Time | Interaction |
| Days 1–3 Through Days 31–70 | Exper. 14.59 Control 19.23 | 0.0022 | 0.1321 | 0.1961 |
| Days 1–7 Through Days 31–70 | Exper. 14.55 Control 19.98 | 0.0002 | 0.0389 | 0.7807 |

In accordance with the protocol of the trial, a cellulosic membrane source was rinsed thoroughly in distilled water, heated to 100° C. for 30 minutes in 2% sodium bicarbonate and 1% ethylenediaminetetraacetic acid solution, then cooled and stored at 4° C. in 2% formaldehyde. The treated cellulosic membrane was rinsed twice in a balanced saline solution and then was cut into appropriate forms. The devices were placed in one eye of New Zealand White rabbits while the other eye served as a control with glaucoma filtering surgery only. The foot portion was passed through a hole in the limbus that was created by excision of a 2–3 mm (width)×0.5 mm (height) section of the scleral wall at the 1:00 o'clock position for placement in the anterior chamber. The body portion of the device was placed in the surgical bed under the scleral flap. The scleral flap was sutured with one or two 8/0 chromic collagen sutures. The conjunctiva was closed using 6/0 nylon or silk sutures. Peripheral iridotomies were not needed. The surgical procedure typically lasted 20 to 30 minutes, and several refinements were made in the course of the study. The foot of the device was buried deep in the angle of the anterior chamber in all the rabbits except Rabbit No. 1. The foot of the device in Rabbit No. 1 was positioned just inside the angle but did not project into the anterior chamber. The intraocular pressures of the eyes of each animal, as measured by pneumotonometry under topical anesthesia, were recorded daily at the same hour. Two investigators independently measured pressures and then averaged the two values. The pressures in the experimental eyes and control eyes were recorded for each animal. Baseline intraocular pressures of the rabbits were measured for three days prior to implant. The rabbits were euthanized at the end of the study and the globes enucleated. The globes were fixed in formaldehyde, processed routinely, and stained with hematoxylin and eosin.

During the 70 day study period, the surgery was followed by direct observation for bleb formation, for surgical effect on the cornea and anterior chamber, and for measurement of intraocular pressure. None of the rabbits developed corneal decompensation, conjunctival erosion or uveitis as a result of the implant. One day postoperatively, the eyes exhibited a slight to moderate intimation of the conjunctiva in the area of the implant. Within seven days, however, the inflammation of the conjunctiva gradually subsided. Immediately after surgery the anterior chambers were flat or normal. Within twenty-four hours normal anterior chambers were formed in all cases. The anterior chamber humor was very clear at three days postoperatively in all rabbits.

The differences between the intraocular pressure of the experimental eye and of the control eye for each of six rabbits over 70 days are shown in Table 1. In the experimental eye group, the daily intraocular pressures were significantly lower than those for the control eye. Only four percent of the daily experimental eye pressure measurements were greater than 19 mmHg while seventy percent of the control eye measurements were greater. Eighty percent of daily experimental eye pressure measurements were between 12-16 mmHg, while in contrast only four percent of the control eye measurements fell within this range. All control eye blebs failed within 14 days, while five of six experimental eyes still maintained a functional filtering bleb at the end of the experiment. The globes were examined by light microscopy. These observations showed that the foot had entered the anterior chamber anterior to the trabecular meshwork. There was no evidence of corneal endothelial damage in any of the globes. Further posteriorly, the body lay within the sclera at a depth of 50 to 60 percent. There was iris touch of the foot in all six experimental eyes, but no necrosis, atrophy or hypertrophy was found.

Rabbit Study No. 2

The invention was implanted in one eye of 10 rabbits and followed for one year. The purposes of this study were to determine if (1) the shape and material of the implant were convenient to use and compatible with living normal eyes; (2) the implant could maintain an open fistula while avoiding immediate hypotony and; (3) the intraocular pressure could be reduced by the device in a normal eye as compared with the contralateral unoperated eye.

All eyes tolerated the implant extremely well and the surgeries were without incident. The anterior chambers reformed quickly and no extraordinary responses were noted. The implants were followed for one year and at this time the eyes were removed and the tissues taken for histological processing.

For this study the implant was constructed from cellulose dialysis membrane stock. The membrane stock was cut by a die into a planar, generally rectangular shape with the dimensions of 6 mm wide by 8 mm long by 0.05 mm thick, while dehydrated.

The finished implants were rinsed in distilled water, then heated to 100° C. for 30 minutes in a solution of 2% sodium bicarbonate and 1% ethylenediuminetetraacetic acid, followed by cooling at 4° C. in balanced saline solution.

The device was implanted beneath a scleral flap (approximately 6×8 mm) with the foot portion passed though a 0.5 mm ×3.0 mm window in the scleral wall at the limbus at the 1:00 position OD and the 11:00 position OS. The foot portion was folded into the anterior chamber and rested in the angle against the trabecular meshwork.

After placement, the body of the implant was covered with a scleral flap then sutured with one or two 8/0 chromic collagen sutures. The conjunctiva was closed with 6/0 nylon or silk sutures. The intraocular pressure of all eyes was measured by pneumotonomentry under topical anesthetic. Measurements of control and experimental eyes were made at the same hour daily for six months then weekly to one year. Two investigators independently measured the pressures and an average was taken.

At termination the eyes were removed and fixed in 10% neutral buffered formaldehyde or 2% paraformaldehyde and 2% glutaraldehyde in cacodylate buffer. After 24 hours of fixation the tissues were processed routinely, sectioned and stained with hematoxylin and eosin. Or alternatively, the eyes were dehydrated, critical point dried and coated with gold for scanning electron microscopy.

The surgical procedure lasted thirty minutes and was performed without incident in all 10 rabbits. After surgery the anterior chamber was rapidly formed and within 24 hours all anterior chambers were deep and clear. The first day post-operatively the eyes showed slight to moderate inflammation of the conjunctiva in the area of the surgery. Within four weeks the inflammation had subsided. The devices remained securely positioned throughout the study and the foot of the implant was visualized by gonioscopy periodically. The formation of a filtering bleb was noted in all cases. None of the eyes developed corneal decompensation, conjunctival erosion or uveitis as a result of this procedure.

Comparing the implanted eye to the untreated control eye, in the first week the implanted eyes had an average IOP of 14 mm Hg as compared with 25 mm Hg in the control eyes. It could be noted that the IOP measurements of the experimental eyes never equaled or exceeded the control eye IOP during 13 months. The individual weekly averages and standard errors of the means are shown in Table 3A-B. Table 4 shows an repeated measures analysis of variance for data presented in Table 3A-B.

TABLE 3A

| Rabbit | Baseline | Wk 1-4 | Wk 5-8 | Wk 9-12 | Wk 13-16 | Wk 17-20 | Wk 21-24 |
| --- | --- | --- | --- | --- | --- | --- | --- |
| 24. Exper. | 30.0 | 16.0 ± 3.0 | 14.5 ± 0.6 | 15.0 ± 1.4 | 16.0 ± 1.4 | 13.6 ± 1.9 | 12.5 ± 3.1 |
| Control | 31.0 | 24.8 ± 2.0 | 21.0 ± 1.4 | 21.5 ± 0.7 | 23.0 ± 1.2 | 21.3 ± 1.2 | 18.0 ± 3.2 |
| 25. Exper. | 27.0 | 12.3 ± 1.4 | 11.4 ± 1.4 | 9.8 ± 2.2 | 11.5 ± 1.7 | 12.9 ± 1.9 | 11.3 ± 1.9 |

TABLE 3A-continued

| Rabbit | | Baseline | Wk 1–4 | Wk 5–8 | Wk 9–12 | Wk 13–16 | Wk 17–20 | Wk 21–24 |
|---|---|---|---|---|---|---|---|---|
| | Control | 26.0 | 22.8 ± 1.0 | 19.9 ± 1.8 | 19.9 ± 1.3 | 21.1 ± 0.8 | 19.6 ± 0.6 | 15.5 ± 0 |
| 26. | Exper. | 24.0 | 15.8 ± 1.2 | 13.8 ± 1.0 | 14.6 ± 0.8 | 13.5 ± 1.5 | 12.3 ± 1.2 | 10.3 ± 2.2 |
| | Control | 25.0 | 23.6 ± 1.9 | 19.5 ± 0.7 | 18.9 ± 1.3 | 19.8 ± 1.3 | 19.4 ± 0.6 | 16.4 ± 2.9 |
| 27. | Exper. | 19.0 | 11.0 ± 1.3 | 10.0 ± 0.4 | 10.8 ± 0.7 | 10.8 ± 0.7 | 13.6 ± 1.1 | 10.6 ± 2.6 |
| | Control | 19.0 | 21.5 ± 1.8 | 16.3 ± 0.9 | 18.6 ± 1.3 | 19.8 ± 0.5 | 20.1 ± 1.0 | 15.3 ± 2.1 |
| 28. | Exper. | 24.0 | 12.0 ± 1.3 | 9.5 ± 0.9 | 13.3 ± 1.5 | 13.1 ± 0.9 | 12.3 ± 1.2 | 11.0 ± 2.0 |
| | Control | 24.0 | 23.8 ± 2.0 | 19.1 ± 0.3 | 20.6 ± 0.9 | 20.6 ± 1.8 | 19.8 ± 1.6 | 15.8 ± 2.9 |
| 29. | Exper. | 23.0 | 14.0 ± 3.4 | 9.0 ± 0.4 | 10.1 ± 0.9 | 12.0 ± 1.2 | 13.3 ± 1.3 | 12.4 ± 1.7 |
| | Control | 25.0 | 19.8 ± 2.5 | 20.3 ± 1.9 | 19.6 ± 2.2 | 20.1 ± 0.8 | 20.3 ± 2.4 | 15.8 ± 1.7 |
| 30. | Exper. | 29.0 | 16.4 ± 1.2 | 15.5 ± 1.7 | 16.3 ± 1.2 | 13.9 ± 0.6 | 13.1 ± 1.0 | 12.3 ± 4.0 |
| | Control | 29.0 | 23.0 ± 2.3 | 20.5 ± 1.0 | 21.4 ± 1.4 | 20.8 ± 1.8 | 19.3 ± 3.1 | 17.9 ± 1.9 |
| 31. | Exper. | 29.0 | 14.6 ± 2.9 | 13.6 ± 2.3 | 12.6 ± 0.5 | 13.1 ± 1.1 | 14.1 ± 0.6 | 12.4 ± 2.3 |
| | Control | 29.0 | 26.4 ± 2.1 | 23.5 ± 2.2 | 23.0 ± 0.9 | 23.0 ± 0.6 | 22.1 ± 1.3 | 18.9 ± 2.2 |
| 32. | Exper. | 30.0 | 11.4 ± 1.5 | 12.0 ± 2.0 | 12.8 ± 0.7 | 11.0 ± 1.2 | 12.1 ± 1.1 | 12.4 ± 1.9 |
| | Control | 30.0 | 21.1 ± 2.9 | 19.5 ± 3.1 | 20.6 ± 1.8 | 20.4 ± 0.9 | 19.0 ± 3.3 | 18.1 ± 1.9 |
| 33. | Exper. | 31.0 | 12.8 ± 1.3 | 10.9 ± 1.6 | 9.9 ± 1.0 | | | |
| | Control | 31.0 | 21.1 ± 2.6 | 19.4 ± 1.3 | 21.8 ± 1.9 | | | |
| 34. | Exper. | 30.0 | 16.8 ± 4.0 | 13.6 ± 2.3 | 13.5 ± 1.8 | 10.6 ± 1.7 | 10.5 ± 0.5 | |
| | Control | 30.0 | 24.7 ± 0.8 | 21.0 ± 1.4 | 22.6 ± 1.3 | 21.0 ± 1.2 | 20.7 ± 0.3 | |
| 35. | Exper. | 29.0 | 14.0 ± 2.5 | 13.6 ± 1.4 | 12.9 ± 0.9 | 12.8 ± 0.7 | 12.8 ± 0.6 | 10.6 ± 2.0 |
| | Control | 29.0 | 23.7 ± 1.1 | 22.4 ± 1.7 | 22.6 ± 2.0 | 21.3 ± 0.5 | 21.4 ± 1.7 | 18.0 ± 4.0 |

TABLE 3B

| Rabbit | | Baseline | Wk 25–28 | Wk 29–32 | Wk 33–36 | Wk 37–40 | Wk 41–44 | Wk 45–48 | Wk 49–52 |
|---|---|---|---|---|---|---|---|---|---|
| 24. | Exper. | 30.0 | 12.5 ± 1.9 | 12.0 ± 2.2 | 14.3 ± 3.8 | 10.8 ± 0.5 | 11.7 ± 0.6 | 12.5 ± 0.6 | 11.5 ± 0.6 |
| | Control | 31.0 | 21.3 ± 3.0 | 20.8 ± 3.0 | 22.5 ± 2.6 | 18.0 ± 0.0 | 18.5 ± 0.4 | 18.1 ± 0.9 | 20.5 ± 1.3 |
| 25. | Exper. | 27.0 | 13.4 ± 0.8 | 13.5 ± 0.7 | | | | | |
| | Control | 26.0 | 20.1 ± 4.0 | 19.5 ± 0.7 | | | | | |
| 26. | Exper. | 24.0 | 12.4 ± 1.5 | 12.8 ± 1.7 | 13.0 ± 2.5 | 10.5 ± 0.6 | 12.3 ± 1.0 | 14.0 ± 0.0 | 17.5 ± 1.3 |
| | Control | 25.0 | 18.0 ± 1.8 | 19.0 ± 1.2 | 19.8 ± 3.1 | 18.5 ± 0.6 | 18.8 ± 0.5 | 17.5 ± 0.6 | 22.0 ± 0.8 |
| 27. | Exper. | 19.0 | 11.4 ± 2.1 | 12.5 ± 1.9 | 13.5 ± 1.3 | 12.0 ± 0.0 | 13.0 ± 0.8 | 14.0 ± 0.0 | 10.0 ± 0.0 |
| | Control | 19.0 | 18.0 ± 3.2 | 19.3 ± 3.3 | 20.0 ± 2.9 | 20.5 ± 0.6 | 20.8 ± 0.5 | 20.0 ± 0.0 | 20.0 ± 0.8 |
| 28. | Exper. | 24.0 | 11.4 ± 1.4 | 13.0 ± 1.8 | 11.8 ± 1.0 | 13.5 ± 1.3 | 14.5 ± 1.3 | 12.0 ± 0.0 | 9.0 ± 0.8 |
| | Control | 24.0 | 15.3 ± 1.7 | 21.3 ± 1.7 | 20.5 ± 2.7 | 18.8 ± 1.7 | 22.5 ± 0.6 | 21.3 ± 1.7 | 22.5 ± 0.6 |
| 29. | Exper. | 23.0 | 13.3 ± 0.9 | 13.8 ± 2.1 | 13.0 ± 1.8 | 11.5 ± 0.6 | 13.3 ± 0.5 | 15.0 ± 0.0 | 11.0 ± 1.8 |
| | Control | 25.0 | 19.8 ± 3.1 | 20.3 ± 2.2 | 2.08 ± 2.8 | 19.5 ± 0.6 | 20.5 ± 0.6 | 19.5 ± 0.6 | 17.5 ± 0.5 |
| 30. | Exper. | 29.0 | 12.8 ± 1.0 | 12.8 ± 2.1 | 14.3 ± 1.0 | 15.8 ± 0.5 | 15.3 ± 0.5 | 16.8 ± 2.1 | 14.0 ± 1.8 |
| | Control | 29.0 | 18.4 ± 1.8 | 19.0 ± 2.6 | 19.0 ± 1.8 | 22.0 ± 0.8 | 20.5 ± 1.3 | 20.0 ± 1.8 | 18.0 ± 1.4 |
| 31. | Exper. | 29.0 | 13.1 ± 1.7 | | | | | | |
| | Control | 29.0 | 20.6 ± 0.5 | | | | | | |
| 32. | Exper. | 30.0 | 13.6 ± 1.5 | 13.3 ± 1.7 | 13.0 ± 1.2 | 13.5 ± 0.6 | 13.3 ± 0.5 | 13.5 ± 0.6 | 14.0 |
| | Control | 30.0 | 20.0 ± 2.4 | 20.5 ± 1.0 | 17.5 ± 1.0 | 18.8 ± 0.5 | 19.0 ± 0.0 | 19.3 ± 1.5 | 22.0 |
| 33. | Exper. | 31.0 | | | | | | | |
| | Control | 31.0 | | | | | | | |
| 34. | Exper. | 30.0 | | | | | | | |
| | Control | 30.0 | | | | | | | |
| 35. | Exper. | 29.0 | 12.0 ± 2.8 | 15.3 ± 1.9 | 11.3 ± 1.9 | 10.0 ± 0.0 | 11.3 ± 0.5 | 12.3 ± 2.1 | 13.0 |
| | Control | 29.0 | 20.4 ± 3.5 | 22.3 ± 3.3 | 18.8 ± 1.9 | 18.5 ± 1.9 | 19.5 ± 0.6 | 21.3 ± 1.5 | 20.0 |

TABLE 3A(2)

(Weeks 1–24)

| Group Means 1 S.D. | Baseline | Wk 1–4 | Wk 5–8 | Wk 9–12 | Wk 13–16 | Wk 17–20 | Wk 21–24 |
|---|---|---|---|---|---|---|---|
| Exper. | 27.1 ± 3.7 | 13.9 ± 2.0 | 12.3 ± 2.1 | 12.6 ± 2.1 | 12.6 ± 1.6 | 12.8 ± 1.0 | 11.6 ± 0.9 |
| Control | 27.3 ± 3.6 | 23.0 ± 1.9 | 20.2 ± 1.8 | 20.9 ± 1.5 | 21.0 ± 1.1 | 20.3 ± 1.0 | 17.0 ± 1.3 |
| Paired t-Test Results | | | | | | | |
| d | −0.2500 | −9.1000 | −7.9167 | −8.2917 | −8.4182 | −7.4909 | −5.3900 |
| t– | −1.1489 | −16.4857 | −147246 | −12.7725 | −20.4849 | −21.8836 | −14.6824 |
| p= | 0.27496 | <0.00000 | <0.00000 | <0.00000 | <0.00000 | <0.00000 | <0.00000 |

TABLE 3B(2)

(Weeks 25-52)

| Group Means 1 S.D. | Wk 25-28 | Wk 29-32 | Wk 33-36 | Wk 37-40 | Wk 41-44 | Wk 45-48 | Wk 49-52 |
|---|---|---|---|---|---|---|---|
| Exper. | 19.2 ± 1.8 | 20.0 ± 1.1 | 19.9 ± 1.5 | 19.3 ± 1.5 | 20.0 ± 1.3 | 19.6 ± 1.4 | 20.3 ± 1.9 |
| Control | 12.6 ± 0.8 | 13.2 ± 0.9 | 13.0 ± 1.1 | 12.2 ± 1.9 | 13.1 ± 1.3 | 13.8 ± 1.6 | 12.5 ± 2.7 |
| Paired t-Test Results | | | | | | | |
| d | −6.6000 | −7.0000 | −6.8375 | −7.1250 | −6.9250 | −5.8625 | −7.8125 |
| t− | −14.6606 | −21.6311 | −12.4691 | −14.8827 | −17.9931 | −7.2837 | −7.1709 |
| p= | <0.00000 | <0.00000 | <0.00000 | <0.00000 | <0.00000 | <0.00000 | <0.00000 |

TABLE 4

Repeated measures analysis of variance for data presented in Table 3

| Data included in Model | Mean IOP (Treatment) | | P Values | |
|---|---|---|---|---|
| | | Treatment | Time | Interaction |
| Weeks 1-4 Through Weeks 9-12 | Exper. 12.95 Control 21.38 | 0.0000000 | 0.0000002 | 0.1948680 |
| Weeks 1-4 Through Weeks 49-52 | Exper. 12.83 Control 19.93 | 0.0000002 | 0.0000286 | 0.0028497 |

It is clearly shown that the experimental group was permanently altered to a lower intraocular pressure. At the end of the experiment all eyes maintained a functional filtering site and the fistula was well open as shown by gonioscopy.

Scanning electron microscopic evaluation of the implant sites showed that the foot portion of the device had entered the anterior chamber at the limbus anterior to the trabecular meshwork. However, there was no evidence of corneal endothelial damage. The foot portion touched the iris, but there was no evidence of necrosis, atrophy or hypertrophy. The body of the device lay in the episcleral space under a thin fibrovascular layer of tissues. There was no evidence of a thin walled, fluid containing bleb as seen with other types of devices, standard filtering surgery or with laser sclerostomy.

Cat Study

The cat study was run on subjects in which both eyes were glaucomatous to a pressure of approximately 33 mm Hg. One eye was implanted with the invention and followed with the untreated control for 29 weeks. After this time, the second eye was implanted and both eyes continued to be monitored for IOP and clarity. It was clearly seen that the IOP of the first treated eyes dropped to approximately 15 mm Hg and remained there for 29 weeks. After the implant surgery was performed on the remaining eye, the same drop in IOP was seen.

Human Studies

The device was so consistently effective in animals and devoid of complications, that human experimental studies were conducted in China. Twenty-three patients, averaging over 60 mm of IOP, were implanted with the present invention. Virtually every case was a severe case, as the patients, who averaged under 50 years of age, had failed to respond to all other conventional medical treatment and had few, if any, alternatives available. Table 5 details individual patient data prior to surgery and up to 60 days postsurgery. Two patients were dropped from the study due to trauma not associated with the device or procedure. Twenty-one patients continue to be monitored. All surgeries were successful.

TABLE 5

| Patient | Starting | 3 days Post-Op | 2 month Post-Op | Note |
|---|---|---|---|---|
| A(F) | 81 mmHg | A.C. shallowing | 14 mmHg | Day 11, Normal AC |
| B(M) | 50 mmHg | A.C. shallowing | 17 mmHg | Day 7, Normal AC |
| C(M) | 80 mmHg | 10 mmHg | Patient feeling very well, no back | |
| D(M) | 80 mmHg | 10 mmHg | 14 mmHg | |
| E(F) | 60 mmHg | 11 mmHg | 14 mmHg | Bleeding AC (1-5) |
| F(F) | 57 mmHg | 9 mmHg | 15 mmHg | |
| G(M) | 75 mmHg | 10 mmHg | 16 mmHg | |
| H(M) | 66 mmHg | 11 mmHg | 18 mmHg | |
| I(M) | 60 mmHg | 10 mmHg | 14 mmHg | |
| J(M) | 72 mmHg | 18 mmHg | 14 mmHg | Red Blood cell in aqueous for first week |
| K(M) | 31 mmHg | 10 mmHg | 13 mmHg | Cataract |
| L(M) | 75 mmHg | 10 mmHg | 15 mmHg | |
| M(M) | 55 mmHg | A.C. shallowing for 11 days, needling bleb when post 1 month | | |
| N(F) | 60 mmHg | 7 mmHg | 14 mmHg | |
| O(M) | 52 mmHg | 14 mmHg | 20 mmHg | |
| P(M) | 51 mmHg | A.C. shallowing for 10 days | 14.mmHg | |
| Q(M) | 90 mmHg | 10 mmHg | 25 mmHg | |
| R(M) | 38 mmHg | 6 mmHg | 14 mmHg | |
| S(M) | 47 mmHg | 9 mmHg | 15 mmHg | |
| T(M) | 81 mmHg | 10 mmHg | 14 mmHg | |
| U(M) | 79 mmHg | 7 mmHg | 14 mmHg | |
| U(F) | 75 mmHg | 15 mmHg | 20 mmHg | |
| W(M) | 75 mmHg | 10 mmHg | Day 16, needling vault bleb | |

The mean IOPs were reduced to 12 mm Hg by the third day (n=23) and have remained low through 60 days. Of the 18 patients who at this time have come in for follow up after three and four months, the IOP has held at 60 day values with no complications. There was no evidence of the immediate absolute hypotony seen in other devices and there were no complications, with all patients experiencing greatly increased comfort. In all cases anterior chambers were full and deep by the seven day exam.

Discussion

The purpose of these studies was to investigate the safety and efficacy of the present invention. It was believed that prior devices had been constructed and implanted with the wrong logic. The aim of the present invention was to create an implant and procedure that enlarged the natural filtration system by inducing a fibrovascular capsule that would not have to remain as a thin bleb. Most prior devices were based on the principle that aqueous humor could be dumped directly from the anterior chamber to the subconjunctival space in a free-flowing manner. This creates a large, thin bleb at the exit site and closure of the fistula to the tube size. Because of frequent failure due to postoperative hypotony and secondary scarring around the blebs and around the aqueous egress ports, it was necessary to construct an implant that provided diffusion through the body of the device as well as its surface. Some investigators have modified the procedures and devices presently available in order to reduce the post-operative hypotony. The major modifications have been in the use of the Molteno device. They are: (1) using viscoelastic substances in the anterior chamber, (2) surgically placing the tube and the body in two separate operations, (3) tying an absorbable suture around the tube that loosens as it dissolves thereby allowing the flow of aqueous to proceed slowly, (4) placing a suture in the lumen of the tube and subsequently removing it in a second operation, and (5) burying the distal end of the tube of the scleral bed of a standard trabeculectomy flap. Generally speaking, most of these devices and modifications failed due to the wound healing response which scars down the sub-conjunctival bleb. This problem is exacerbated by the extensive dissection of tissue necessary to position the larger implants that not only stimulates the wound healing response but is continually irritated by the interference with eye movement and muscle tension.

These studies shows that an implant constructed from cellulose dialysis membrane stock increased the filtration rate of aqueous humor even in normal eyes. This surgery was simple and the cellulose device had no toxicity or inflammatory properties. The device is small, does not interfere with eye movement and as a result, did not produce irritation from muscle tension. The animal studies further showed that the implant produced a significant drop in the intraocular pressure that was maintained through one year while the eyes remained quiet and normal appearing.

Many advantages are obtained through the use of the method and apparatus of the present invention. As the implant is designed to permit the regulated flow of fluids through it, aqueous drainage is achieved in a consistent and predictable fashion. Additionally, the placement of the device in the limbal opening virtually eliminates closure by both immediate and chronic tissue responses. Further, the need for a peripherial iridotomy is abolished, thereby reducing the risk of vitreous damage.

More advantages are gained by the composition of, and shape of, the implant. As the implant is constructed of a cellulosic membrane, it is easy to form and may be pre-manufactured to varying dimensions at a low cost. It is also non-toxic to eye tissue and can be sterilized by boiling or autoclave. The flat profile and flaccid nature of the device work to reduce friction and wear on the scleral flap and promote the conformation of the device to the natural curvature of the eye without imparting a mechanical resistance which could produce scleral erosion or a change in eye curvature. Also owing to its shape, the device functions to form a fistula and the body of the implant forms the filtration area. Because the foot portion of the implant sets in the anterior chamber, it works to keep the entrance to the fistula open. Additionally, the design of the implants inhibits forward or backward displacement. Still further, because proximal end of the implant is center cut, the necessary size of the limbal opening is reduced. This feature also helps to lessen the occurrence of post surgical hypotony and the chance of iris endothelium irritation upon insertion of the foot portion of the implant into the anterior chamber.

While the invention has been described with a certain degree of particularity, it is manifest that many changes may be made in the details of construction and the arrangement of components without departing from the spirit and scope of this disclosure. It is understood that the invention is not limited to the embodiment set forth herein for purposes of exemplification, but is to be limited only by the scope of the attached claim or claims, including the full range of equivalency to which each element thereof is entitled.

What is claimed is:

1. An implant for lowering the intraocular pressure of an eye which comprises a planar cellulosic membrane shaped and adapted to extend from the anterior chamber of the eye through an opening in the limbus cornea to a drainage area beneath a scleral flap.

2. The implant according to claim 1, wherein said cellulosic membrane consists essentially of a homopolymer of glucose units connected in a 1,4'-β linkage.

3. The implant according to claim 1, wherein said implant is of a generally rectangular shape having a proximal end, a distal end, and outer margins.

4. The implant according to claim 3, wherein said margins of said implant toward said proximal end form a foot portion for placement in the anterior chamber of the eye and a body portion opposed to said foot portion for burial beneath the scleral flap.

5. The implant according to claim 4, wherein said implant has a center cut axially extending from said proximal end toward said distal end such that said foot portion can be folded for easy insertion through the opening in the limbus corneae.

6. The implant according to claim 4, wherein two opposing rectangular notches are formed in said margins toward said proximal end so as to form said foot portion.

7. The implant according to claim 4, wherein said implant is of a thickness of approximately 25–150 microns.

8. The implant according to claim 7, wherein the overall length of said implant is approximately 8–10 mm and the overall width is approximately 6 mm.

9. An implant for lowering the intraocular pressure of an eye which comprises a cellulosic membrane consisting essentially of a homopolymer of glucose units connected in a 1,4'-β linkage adapted to extend from the anterior chamber of the eye through an opening in the limbus corneae to a drainage area beneath a scleral flap, said implant being of a planar, generally rectangular shape and having a proximal end, a distal end, and outer margins, said margins toward said proximal end forming a foot portion for placement in the anterior chamber and a body portion opposed to said foot portion for burial beneath the scleral flap, said implant having a center cut axially extending from said proximal end toward said distal end such that said foot portion can be folded for easy insertion through the opening in the limbus corneae.

10. The implant according to claim 9, wherein said implant is of a thickness of approximately 25–150 microns.

11. The implant according to claim 10, wherein the overall length of said implant is approximately 8–10 mm and the overall width is approximately 6 mm.

12. The implant according to claim 9, wherein two opposing rectangular notches are formed in said margins toward said proximal end so as to form said foot portion.

13. The implant according to claim 12, wherein said foot portion has a length of approximately 1 mm and a width of approximately 6 mm, said two opposing rectangular notches measure approximately 1 mm in length and 1.5 mm in width, and said body portion has a length of approximately 8 mm and a width of approximately 6 mm.

14. The implant according to claim 9, wherein said foot portion is provided with at least one curved, resilient arm member radially extending therefrom for abutting the inner surface of the limbus corneae after implantation so as to maintain the post-surgical position of said implant.

15. The implant according to claim 14, wherein said arm member is formed of polypropylene and is glued to said foot portion with a cyanoacrylate surgical adhesive.

16. The implant according to claim 14, wherein said arm member is formed of polymethylacrylate and is polymerized integrally to said foot portion.

17. An implant for lowering the intraocular pressure of an eye which comprises a cellulosic membrane consisting essentially of a homopolymer of glucose units connected in a 1,4'-β linkage adapted to extend from the anterior chamber of the eye through an opening in the limbus corneae to a drainage area beneath a scleral flap, said implant being of a planar, generally rectangular shape and having a proximal end and a distal end, said proximal end having an integrally formed key projecting therefrom for placement through said opening and into said anterior chamber, said key having at least one curved, resilient arm member radially extending therefrom for abutting the inner surface of the limbus corneae after implantation so as to maintain the post-surgical position of said implant.

18. The implant according to claim 17, wherein said key is center cut to divide said key into a first piece and a second piece such that said key can be folded for easy insertion through the opening in the limbus corneae.

19. The implant according to claim 18, wherein said key has two curved, resilient arm members, a first arm member radially extending from said first piece and a second arm member radially extending from said second piece.

20. The implant according to claim 17, wherein said arm member is formed of polypropylene and is glued to said key with a cyanoacrylate surgical adhesive.

21. The implant according to claim 17, wherein said arm member is formed of polymethylacrylate and is polymerized integrally to said key.

22. A method for lowering the intraocular pressure of an eye, which comprises positioning an implant within the eye such that said implant comprises a pre-formed cellulosic membrane, said membrane extends from the anterior chamber of the eye through an opening in the limbus cornea to a drainage area beneath a scleral flap.

23. The method according to claim 22, wherein said cellulosic membrane consists essentially of a homopolymer of glucose units connected in a 1,4'-β linkage.

24. The method according to claim 23, wherein said implant is of a planar, generally rectangular shape having a proximal end, a distal end, and outer margins, said margins toward said proximal end forming a foot portion for placement in the anterior chamber and a body portion opposed to said foot portion for burial beneath the scleral flap.

25. The method according to claim 24, wherein said implant has a center cut axially extending from said proximal end toward said distal end such that said foot portion can be folded for easy insertion through the opening in the limbus corneae.

26. The method according to claim 24, wherein said implant is of a thickness of approximately 25–150 microns.

27. The method according to claim 24, wherein the overall length of said implant is approximately 8–10 mm and the overall width is approximately 6 mm.

28. The method according to claim 24, wherein two opposing rectangular notches are formed in said margins toward said proximal end so as to form said foot portion.

29. The method according to claim 28, wherein said foot portion has a length of approximately 1 mm and a width of approximately 6 mm, said two opposing rectangular notches measure approximately 1 mm in length and 1.5 mm in width, and said body portion has a length of approximately 8 mm and a width of approximately 6 mm.

30. The method according to claim 24, wherein said foot portion is provided with at least one curved, resilient arm member radially extending therefrom for abutting the inner surface of the limbus corneae after implantation so as to maintain the post-surgical position of said implant.

31. The method according to claim 30, wherein said arm member is formed of polypropylene and is glued to said foot portion with a cyanoacrylate surgical adhesive.

32. The method according to claim 30, wherein said arm member is formed of polymethylacrylate and is polymerized integrally to said foot portion.

33. A method for lowering the intraocular pressure of an eye, which comprises positioning an implant within the eye such that said implant extends from the anterior chamber of the eye through an opening in the limbus corneae to a drainage area beneath a scleral flap, said implant comprising a pre-formed cellulosic membrane consisting essentially of a homopolymer of glucose units connected in a 1,4'-β linkage, said implant being of a planar, generally rectangular shape and having a proximal end and a distal end, said proximal end having an integrally formed key projecting therefrom for placement through said opening and into said anterior chamber, said key having at least one curved, resilient arm member radially extending therefrom for abutting the inner surface of the limbus corneae after implantation so as to maintain the post-surgical position of said implant.

34. The method according to claim 33, wherein said key is center cut to divide said key into a first piece and a second piece such that said key can be folded for easy insertion through the opening in the limbus corneae.

35. The method according to claim 34, wherein said key has two curved, resilient arm members, a first arm member radially extending from said first piece and a second arm member radially extending from said second piece.

36. The method according to claim 33, wherein said arm member is formed of polypropylene and is glued to said key with a cyanoacrylate surgical adhesive.

37. The method according to claim 33, wherein said arm member is formed of polymethylacrylate and is polymerized integrally to said key.

38. A method for lowering the intraocular pressure of an eye, which comprises the steps of:
(a) die cutting a cellulosic membrane into a planar, generally rectangular shape to form an implant, said implant having a proximal end, a distal end, and outer margins, said margins toward said proximal end being altered so as to form a foot portion and a body portion;
(b) thoroughly rinsing said cellulosic membrane in distilled water;
(c) heating said cellulosic membrane to 100° C. for 30 minutes in 2% sodium bicarbonate and 1% ethylenediuminetetraacetic acid;
(d) cooling said cellulosic membrane at 4° C. in 2% formaldehyde or balanced saline solution;
(e) rinsing said cellulosic membrane in a balanced saline solution;
(f) implanting said implant within the eye such that said foot portion extends into the anterior chamber of the eye through an opening in the limbus corneae and said body portion is buried beneath a scleral flap.

39. A method for lowering the intraocular pressure of an eye, which comprises the steps of:

(a) making an 8 mm cord length conjunctival incision 8–10 mm posterior to the surgical limbus of the eye in the desired quadrant;

(b) forming a conjunctival flap by dissecting the conjunctiva from Tenon's capsule;

(c) forming a scleral flap by cauterizing an area of the sclera to define the perimeter of said scleral flap, outlining the margins of said scleral flap with partial thickness incisions, and dissecting, starting posteriorly, the outlined sclera to obtain said scleral flap;

(e) positioning an implant within the eye such that said implant extends from the anterior chamber of the eye through the opening in the limbus corneae to a drainage area beneath said scleral flap, said implant comprising a pre-formed cellulosic membrane consisting essentially of a homopolymer of glucose units connected in a 1,4'-β linkage;

(f) suturing said scleral flap and said implant to the sclera; and (g) closing the conjunctiva and Tenon's capsule with sutures.

* * * * *